(12) United States Patent
Bertron et al.

(10) Patent No.: US 7,967,779 B2
(45) Date of Patent: Jun. 28, 2011

(54) POWDER AND LIQUID MIXING SYRINGE

(76) Inventors: Kim W. Bertron, Tallahassee, FL (US); John Wiley Horton, Tallahassee, FL (US); Brian J. Boothe, Raleigh, NC (US)

( * ) Notice: Subject to any disclaimer, the term of this patent is extended or adjusted under 35 U.S.C. 154(b) by 617 days.

(21) Appl. No.: 12/008,510

(22) Filed: Jan. 11, 2008

(65) Prior Publication Data

US 2008/0146998 A1 Jun. 19, 2008

Related U.S. Application Data

(62) Division of application No. 10/909,486, filed on Aug. 2, 2004, now Pat. No. 7,329,235.

(51) Int. Cl.
*A61M 37/00* (2006.01)
*A61M 5/00* (2006.01)
*A61M 5/315* (2006.01)

(52) U.S. Cl. ............. 604/89; 604/87; 604/191; 604/228

(58) Field of Classification Search ............... 604/82–92, 604/181, 187, 218, 232, 191
See application file for complete search history.

(56) References Cited

U.S. PATENT DOCUMENTS

| | | | | |
|---|---|---|---|---|
| 3,477,432 A | * | 11/1969 | Shaw | 604/91 |
| 3,838,689 A | * | 10/1974 | Cohen | 604/90 |
| 5,429,603 A | * | 7/1995 | Morris | 604/88 |

* cited by examiner

*Primary Examiner* — Matthew F DeSanto
(74) *Attorney, Agent, or Firm* — J. Wiley Horton

(57) ABSTRACT

A mixing syringe having a first sealed chamber containing a powder (powder housing) and a second sealed chamber containing a liquid (liquid housing). When the user needs to inject a patient, he or she holds the mixing syringe approximately upright and depresses a plunger. This motion causes a piercer to pierce a foil seal separating the two chambers. The liquid then drops down into the powder housing. The liquid flows through a passage in a piston located in the powder housing, where it then comes in contact with the powder itself. As the user continues pressing the plunger downward, the piercer comes to rest within the piston and seals the passage through the piston, thereby locking the piercer and piston together. The device is then ready for an injection. As the plunger is further depressed, the piston expels the powder and liquid mixture through a needle.

18 Claims, 14 Drawing Sheets

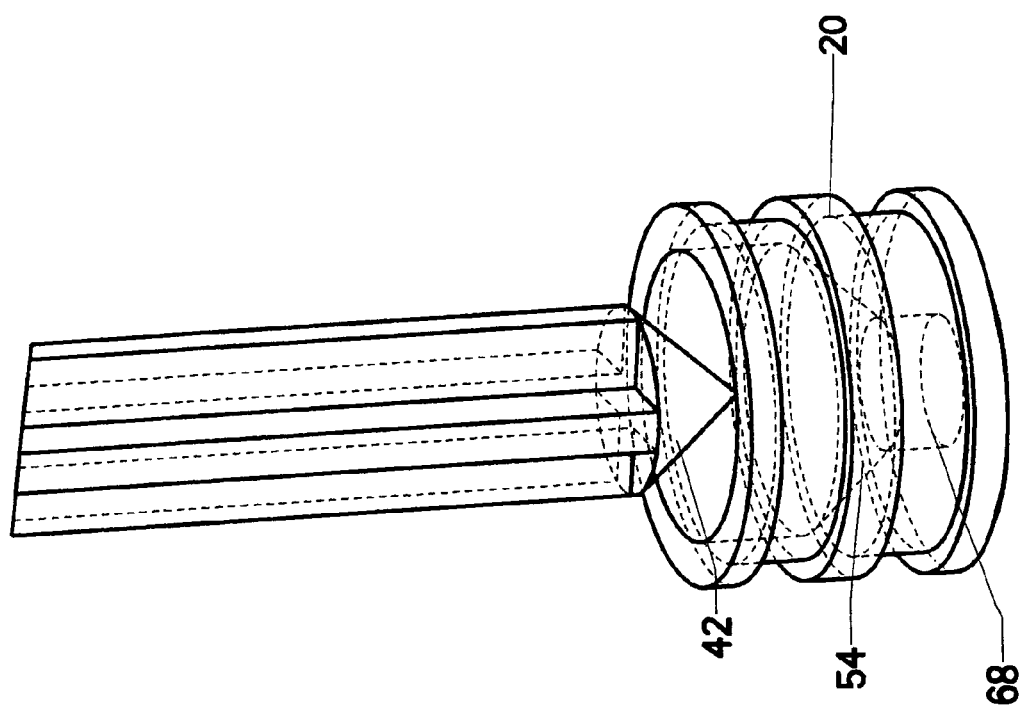

POWDER AND LIQUID MIXING SYRINGE

CROSS-REFERENCES TO RELATED APPLICATIONS

This application is a divisional application claiming the benefit of U.S. application Ser. No. 10/909,486. The earlier application listed the same inventors and was filed on 2 Aug. 2004 now U.S. Pat. No. 7,329,235.

STATEMENT REGARDING FEDERALLY SPONSORED RESEARCH OR DEVELOPMENT

Not Applicable

MICROFICHE APPENDIX

Not Applicable

BACKGROUND OF THE INVENTION

1. Field of the Invention

This invention relates to the field of medical devices. More specifically, the invention comprises a syringe which can mix a powder with a liquid carrier prior to injection into a patient.

2. Description of the Related Art

Syringes have long been used to inject liquid medicinal substances into the human body. Many such medicinal substances can be stored for extended periods in the syringe, ready for use. This is not true for all medicinal substances, however. A significant group of compounds must be stored in crystalline form. The crystalline form is difficult to introduce to the body, so a two step approach has been traditionally used.

The crystalline substance is stored in a small bottle. A carrier liquid—which will be used to form a solution or colloid of the crystalline substance—is stored in a separate syringe. The bottle is provided with a soft cap. The syringe's needle can be inserted through this soft cap. The syringe is then used to inject the carrier liquid into the bottle.

The bottle is then swirled to mix the crystalline substance into the carrier liquid. The syringe is then used to suck the liquid—now containing the crystalline substance—back out of the bottle. Once back in the syringe, the liquid can be injected into the patient in a conventional fashion.

Medical personnel are familiar with this multi-step approach and generally perform the steps without a problem. Certain substances, however, are by their nature destined for use by untrained persons. One good example would be substances intended to treat hypoglycemia, particularly in diabetic persons.

Glucogon is used to treat hypoglycemia. It is particularly effective for diabetics who are experiencing dangerously low blood sugar. An injection of Glucogon can remedy this serious problem. Unfortunately, Glucogon cannot be stored for long periods as a solution or colloid. It must instead be stored as a dry powder. Thus, the multi-step process described previously must be used to prepare and administer a Glucogon injection.

Glucogon must generally be available for emergency use in insulin-dependent diabetics. It is used when the diabetic is showing signs of severe distress. Someone such as a family member must be prepared to give the injection, since time lost waiting for medical personnel or transportation to a hospital can be damaging, if not fatal. The reader will therefore appreciate that the person attempting to administer the Glucogon injection (1) probably has little experience with giving such injections, and (2) is likely to be under considerable emotional stress.

The multi-step process found in the prior art often goes awry in these circumstances. The needle may be bent while trying to penetrate the bottle's cap. Other persons have injected the carrier liquid while omitting the mixing step altogether (which obviously does no good). Thus, a product which simplifies the process of mixing a powder medical product into a carrier liquid prior to injection would be quite helpful.

BRIEF SUMMARY OF THE INVENTION

The present invention comprises a mixing syringe. The syringe has a first sealed chamber containing a powder (powder housing) and a second sealed chamber containing a liquid (liquid housing). When the user needs to inject a patient, he or she holds the mixing syringe approximately upright and depresses a plunger. This motion causes a piercer to pierce a foil seal separating the two chambers. The liquid then drops down into the powder housing. The liquid flows through a passage in a piston located in the powder housing, where it then comes in contact with the powder itself.

As the user continues pressing the plunger downward, the piercer comes to rest within the piston and seals the passage through the piston, thereby locking the piercer and piston together. The syringe is then optionally agitated to promote thorough mixing of the powder and liquid. The device is then ready for an injection. As the plunger is further depressed, the piston expels the powder and liquid mixture through a needle.

BRIEF DESCRIPTION OF THE SEVERAL VIEWS OF THE DRAWINGS

FIG. 1C is a detailed perspective view, showing the primary piston.

REFERENCE NUMERALS IN THE DRAWINGS

| 10 | mixing syringe | 12 | needle |
|----|----|----|----|
| 14 | needle anchor | 16 | powder housing |
| 18 | liquid housing | 20 | primary piston |
| 22 | flange | 24 | flange |
| 26 | foil seal | 28 | foil seal |
| 30 | linking clip | 32 | flange |
| 34 | retaining clip | 36 | bore |
| 38 | bore | 40 | vent block |
| 42 | piercer | 44 | secondary piston |
| 46 | vent | 48 | piercer rod |
| 50 | plunger head | 52 | plunger rod |
| 54 | piercer seat | 56 | powder |
| 58 | needle inlet | 60 | powder assembly |
| 62 | needle cap | 64 | liquid assembly |
| 66 | liquid | 68 | passage |
| 70 | mixing chamber | 72 | escaping air |
| 74 | mixture | 76 | plunger |

DETAILED DESCRIPTION OF THE INVENTION

Figure 1:
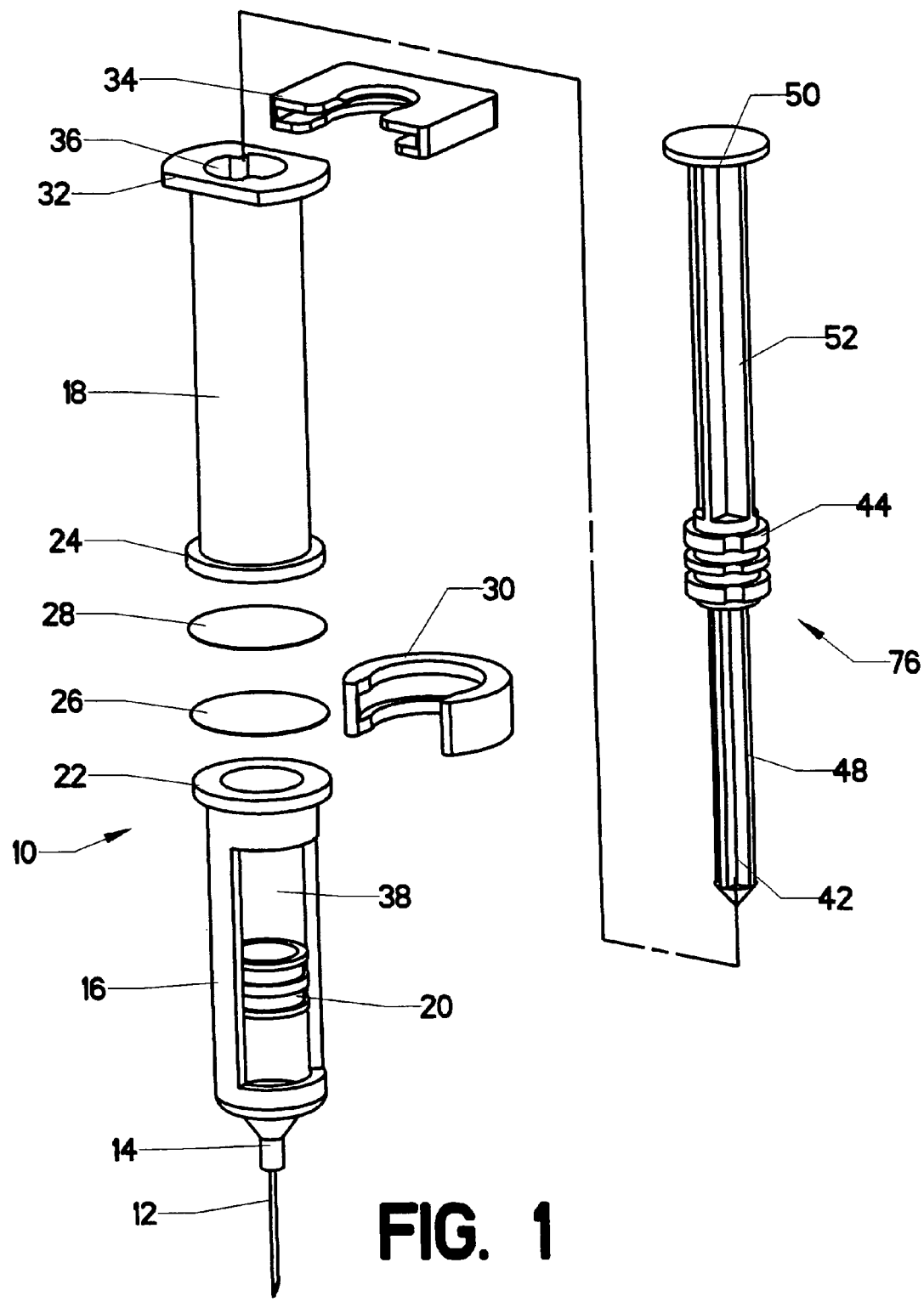
FIG. 1 is an exploded perspective view with a cutaway, showing all the components of the present invention.

FIG. 1 shows all the invention's components in an exploded view. Needle 12 is attached to powder housing 16 at needle anchor 14. The lower portion of the powder housing is fluidly connected with the needle's hollow interior (Throughout this disclosure, directional terms such as "upper" and "lower" will be understood to refer only to the orientations of objects shown in the views, and should not be construed as limitations on the scope of the invention). Bore 38 runs through the center of powder housing 16. Primary piston 20 can slide downward within bore 38, though it is ordinarily held in place by friction and does not move freely.

The upper end of the powder housing 16 is open. Flange 22 surrounds this opening. The opening is ordinarily covered by some type of seal. In the embodiment shown, foil seal 26 is glued to the upper surface of flange 22 in order to seal the opening. The particular construction of the seal is unimportant, so long as it can be pierced (the significance of which will be explained subsequently).

Liquid housing 18 is located above powder housing 16. Bore 36 passes completely through the liquid housing, meaning that both ends of the liquid housing are open. Flange 24 is located on the open lower end of the liquid housing. The lower opening is sealed by gluing foil seal 28 to flange 24.

In assembling the device for use, flange 24 is pressed against flange 22. Linking clip 30 can then be locked over the two flanges to mate liquid housing 18 to powder housing 16. The linking clip is preferably made of a resilient material so that it can "snap" into place. It thereby holds the two housings firmly together.

Plunger 76 is designed to slide into bore 36. Secondary piston 44 slides tightly within the bore. Piercer 42 is a conical surface located well below the secondary piston. Piercer rod 48 locates piercer 42 with respect to secondary piston 44. Plunger head 50 is connected to secondary piston 44 by plunger rod 52. The user actually presses on the plunger head to actuate the device.

Once the plunger is installed within bore 36, it may be desirable to prevent its accidental removal (which may inadvertently release the contents of the liquid housing). Retaining clip 34 is provided to prevent the plunger's removal. It slides over flange 32 and locks into place. The reader will observe that the retaining clip features a center hole which is large enough to allow the passage of plunger rod 52 but not large enough to allow the passage of secondary piston 44.

Thus, with the plunger installed and the retaining clip in position, the user cannot pull the plunger out of the liquid housing.

Figure 1B:
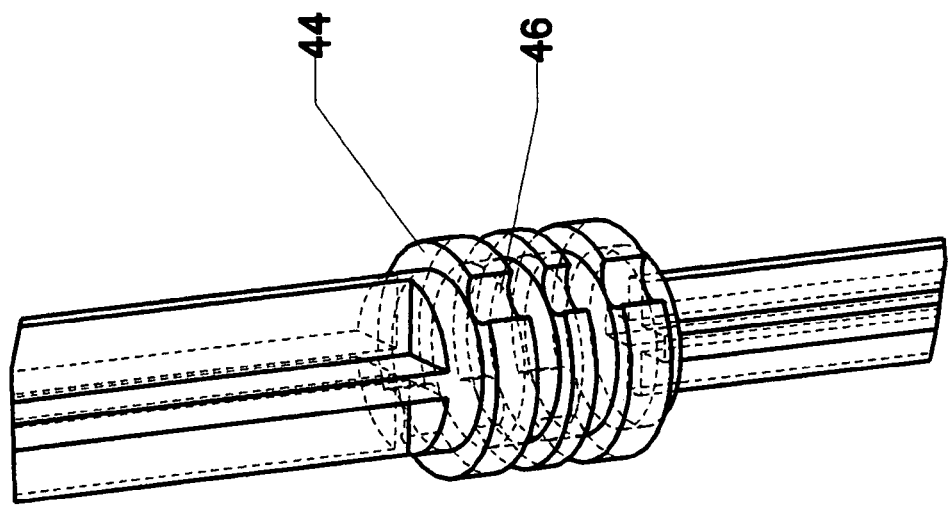
FIG. 1B is a detailed perspective view, showing the secondary piston.
Figure 1B:
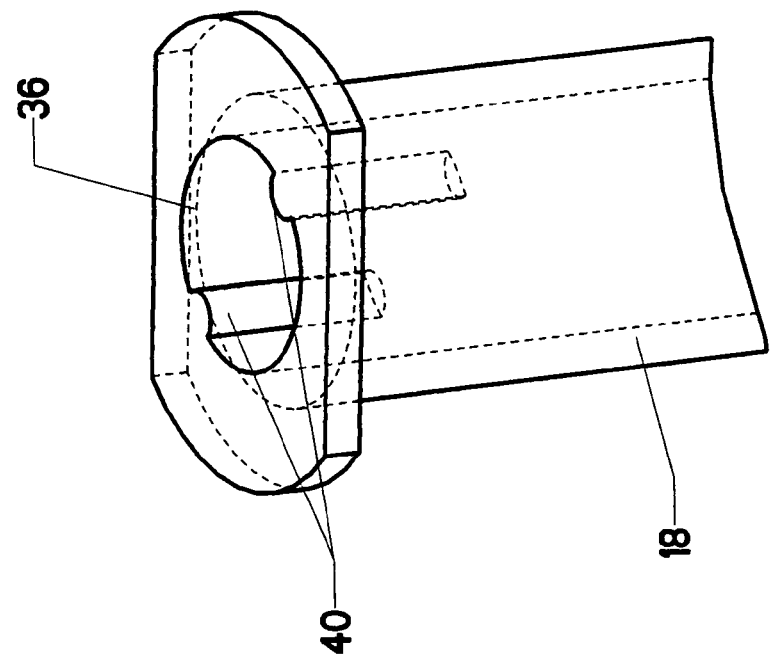

FIGS. 1B and 1C shows certain features in more detail. FIG. 1B shows how the upper portion of bore 36 incorporates a pair of vent blocks 40. The reader will observe that secondary piston 44 incorporates a pair of corresponding vents 46. When the secondary piston is near the top of bore 36, the two vent blocks 40 seal the two vents 46. Thus, when the user presses the plunger downward into the bore, air within the liquid housing cannot escape past the secondary piston. The air must be compressed by the piston. However, once secondary piston 44 has moved downward enough to clear the two vent blocks 40, air can pass through the two vents 46. The operational significance of these features will be explained subsequently.

FIG. 1C shows how piercer 42 interacts with primary piston 20. Primary piston 20 includes a passage 68 which opens into piercer seat 54. Piercer 42 has a male conical shape whereas piercer seat 54 has a female conical shape. Those skilled in the art will realize that if the piercer is pushed against the primary piston, the piercer will seal against the piercer seat, thereby closing passage 68. If the plunger is then depressed further, the piercer will push the primary piston downward.

Figure 2:
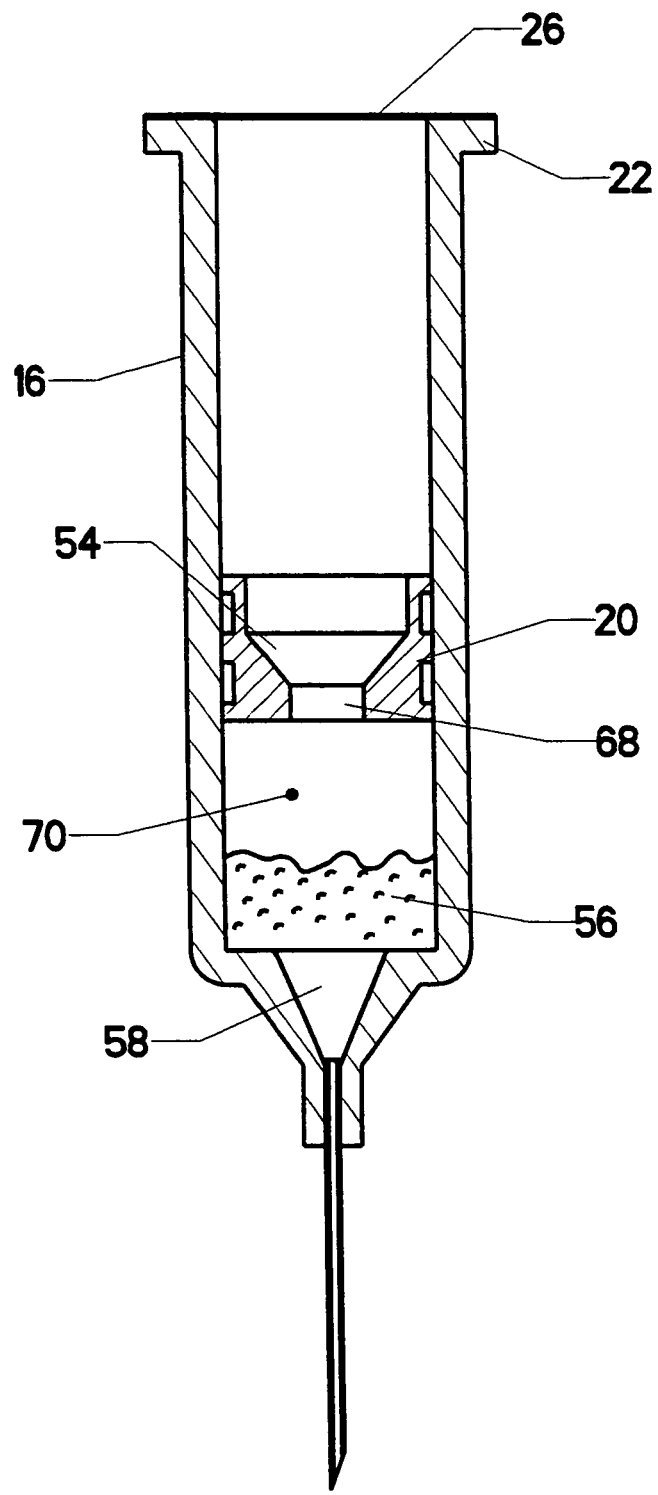
FIG. 2 is a sectional elevation view, showing the powder housing.

FIG. 2 is a sectional elevation view through the powder housing, showing it ready for assembly into a completed syringe. Some explanation of how this component might be manufactured is helpful. The needle is attached to the empty powder housing prior to the addition of any other components. The housing is then oriented upright as shown. Foil seal 26 and primary piston 20 are not yet present. Powder 56 is introduced through the open top and allowed to settle in the bottom. Primary piston 20 is then pushed downward to the position shown, where it will be retained by friction. The area below the primary piston is designated as mixing chamber 70. In this view, the reader can easily perceive the shape of piercer seat 54 and passage 68 in primary piston 20.

Figure 3:
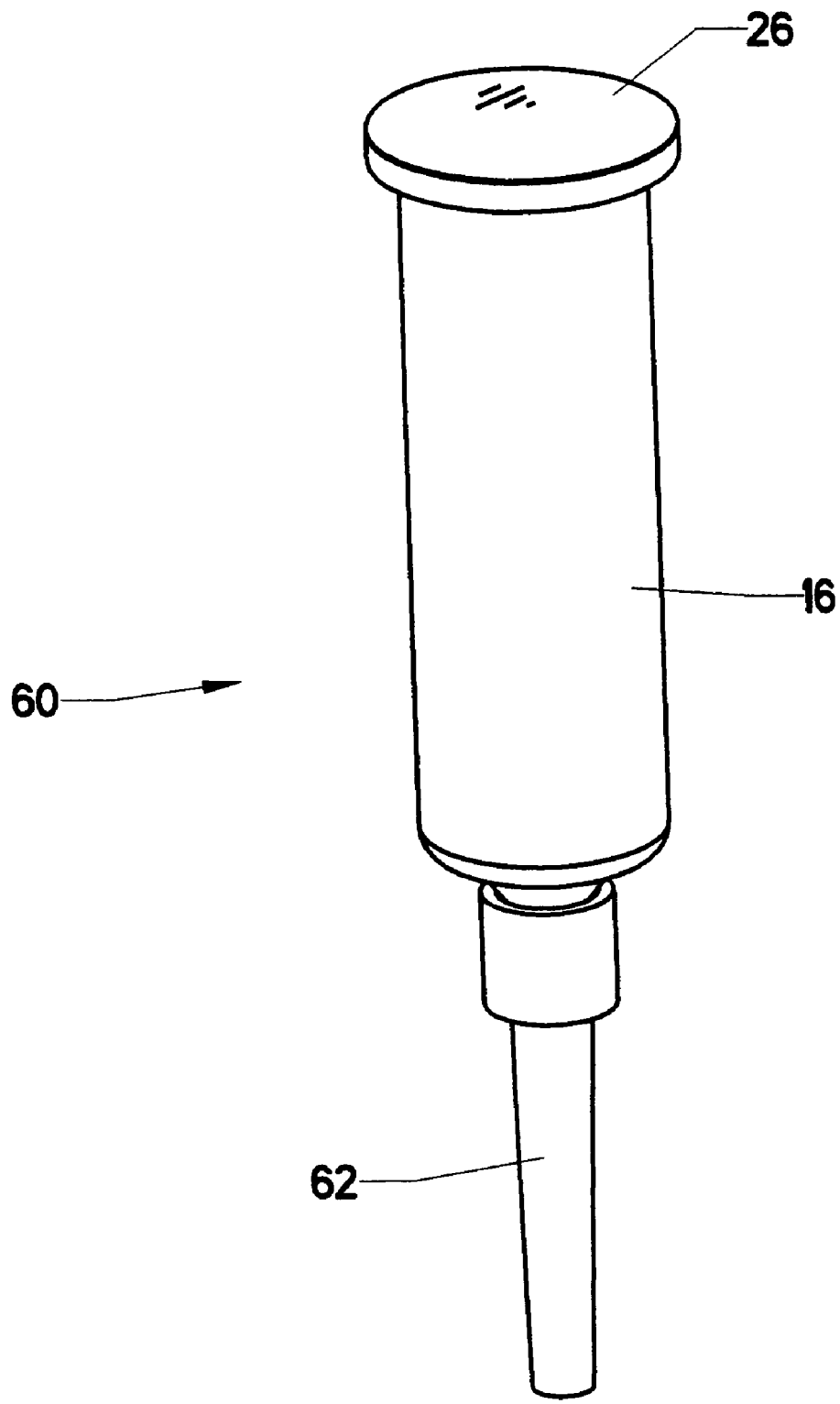
FIG. 3 is a perspective view, showing the powder housing.

Once all the items are placed within the powder housing, the upper opening is sealed by the addition of foil seal 26. FIG. 3 shows the completed powder assembly 60, with foil seal 26 in place. Those skilled in the art will know that many materials could be substituted for the foil seal, such as a thin plastic membrane. Needle cap 62 is shown snapped over the needle in the view. This protects the needle and also protects the user from inadvertent injury. The needle cap is, of course, removed prior to using the syringe.

Figure 4:
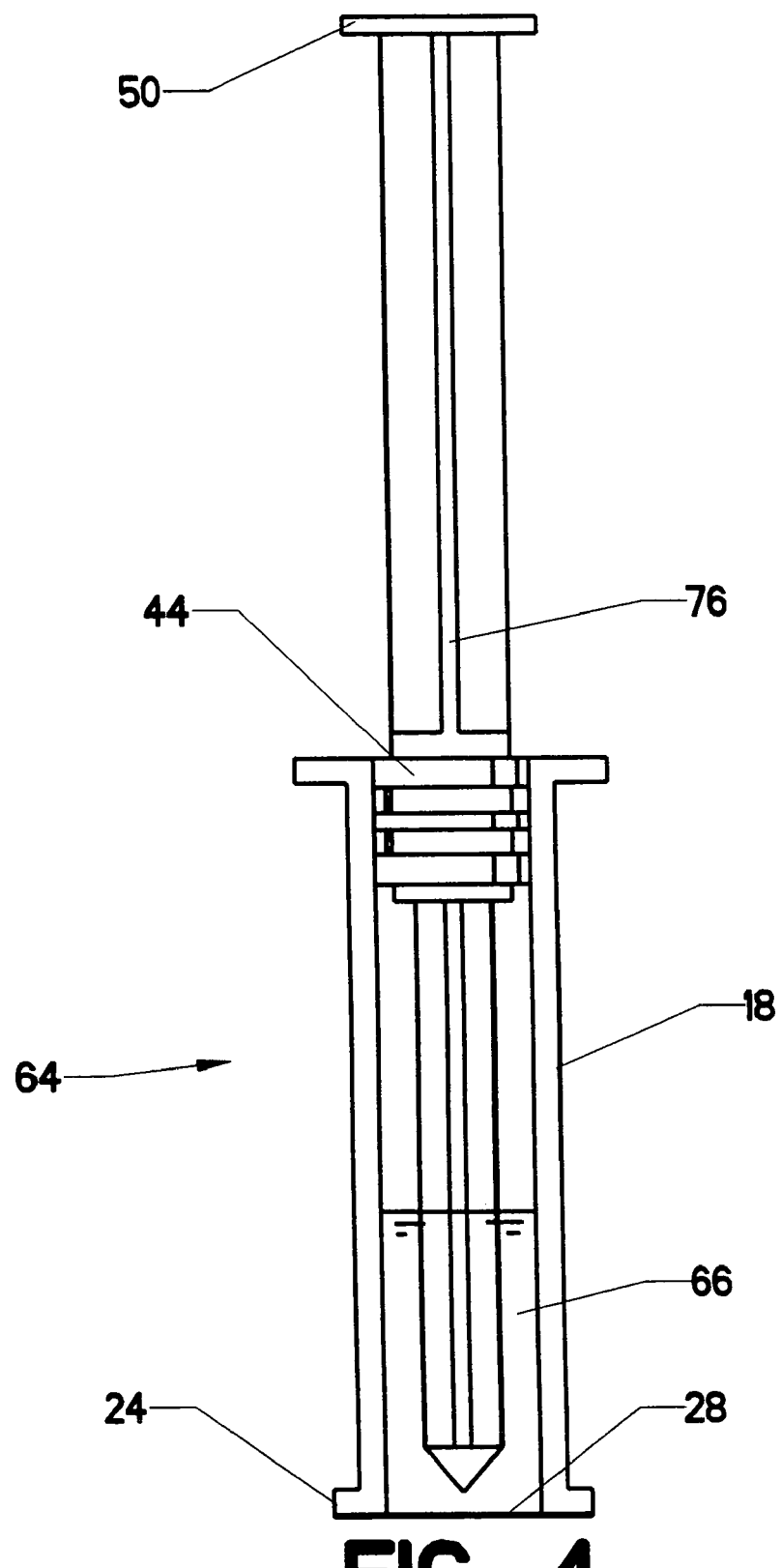
FIG. 4 is a sectional elevation view, showing the liquid housing.

FIG. 4 shows an elevation view through liquid assembly 64. A brief understanding of its manufacturing process may also be helpful. Foil seal 28 is placed over the open lower end of liquid housing 18. A desired volume of liquid 66 is then introduce through its open upper end. Next, plunger 76 is inserted through the open upper end, with secondary piston 44 sealing off the open upper end.

Figure 5:
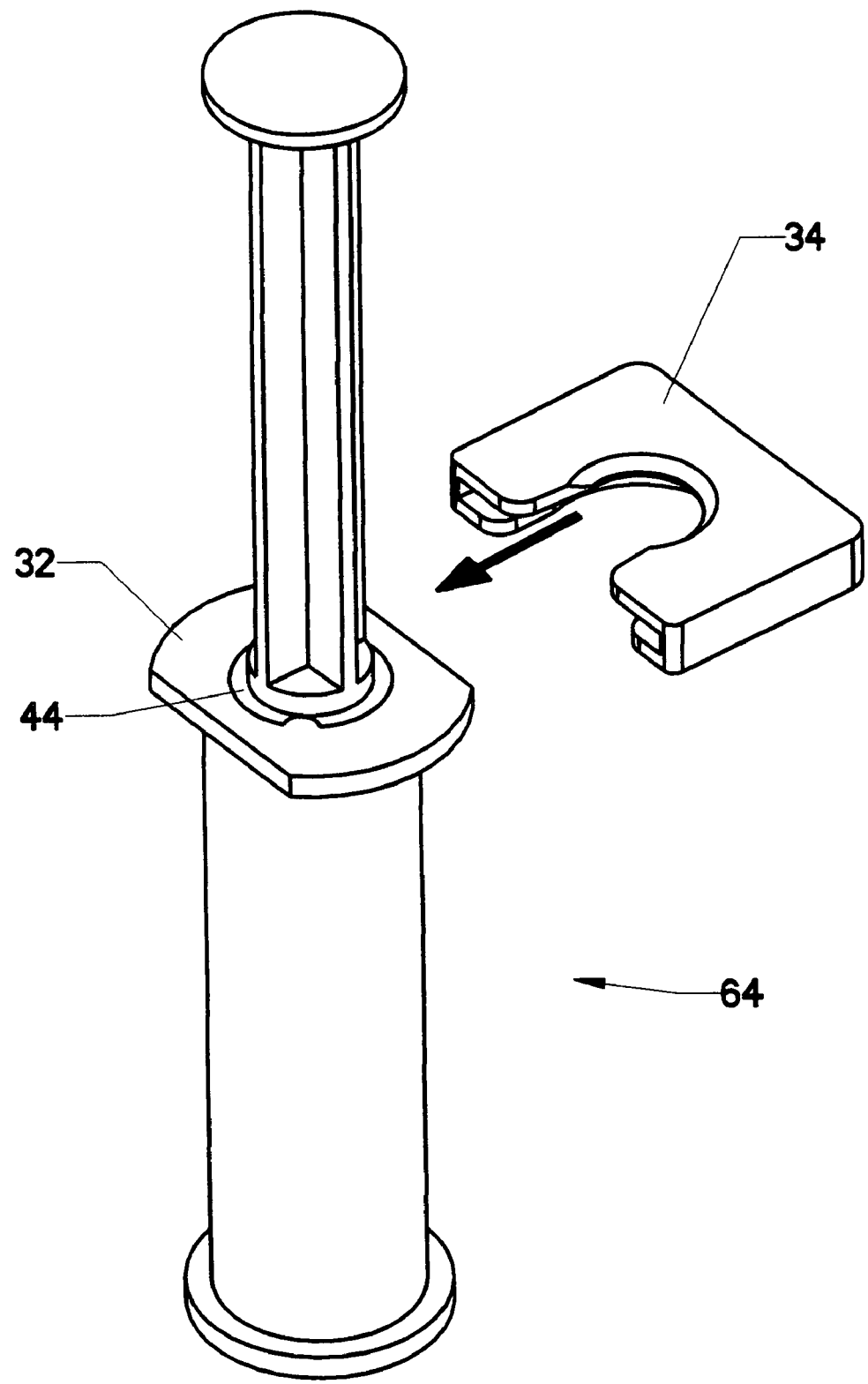
FIG. 5 is a perspective view, showing the liquid housing.

Referring now to FIG. 5, retaining clip 34 can then be locked over flange 32 to retain the plunger within the liquid housing. Liquid assembly 64 is thereby complete. The reader will appreciate that the powder assembly and the liquid assembly can be manufactured on different production lines. They could even be made in completely separate facilities. They need only be united just prior to use.

Figure 6:
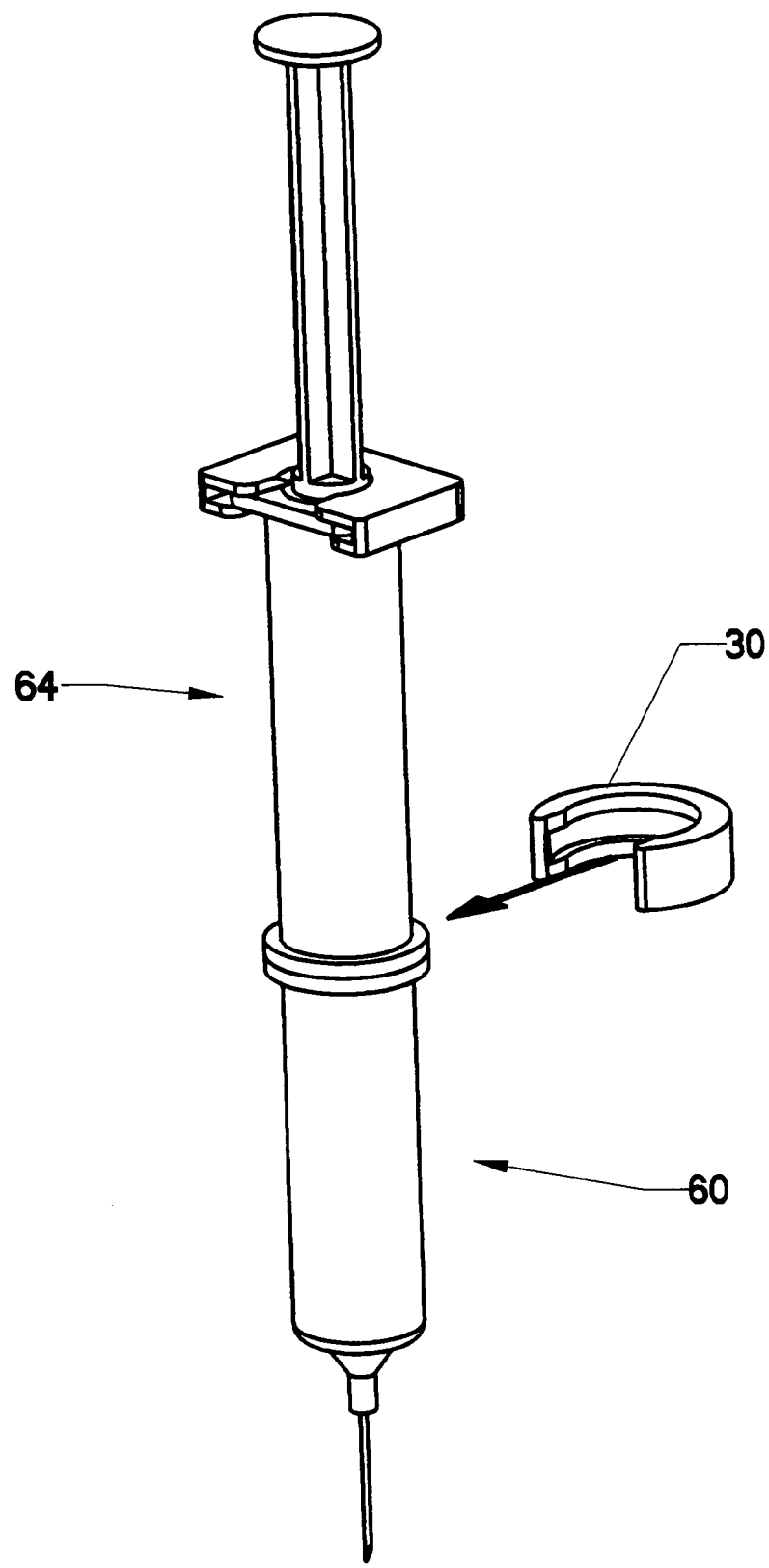
FIG. 6 is a perspective view, showing the liquid and powder housings united.
Figure 7:
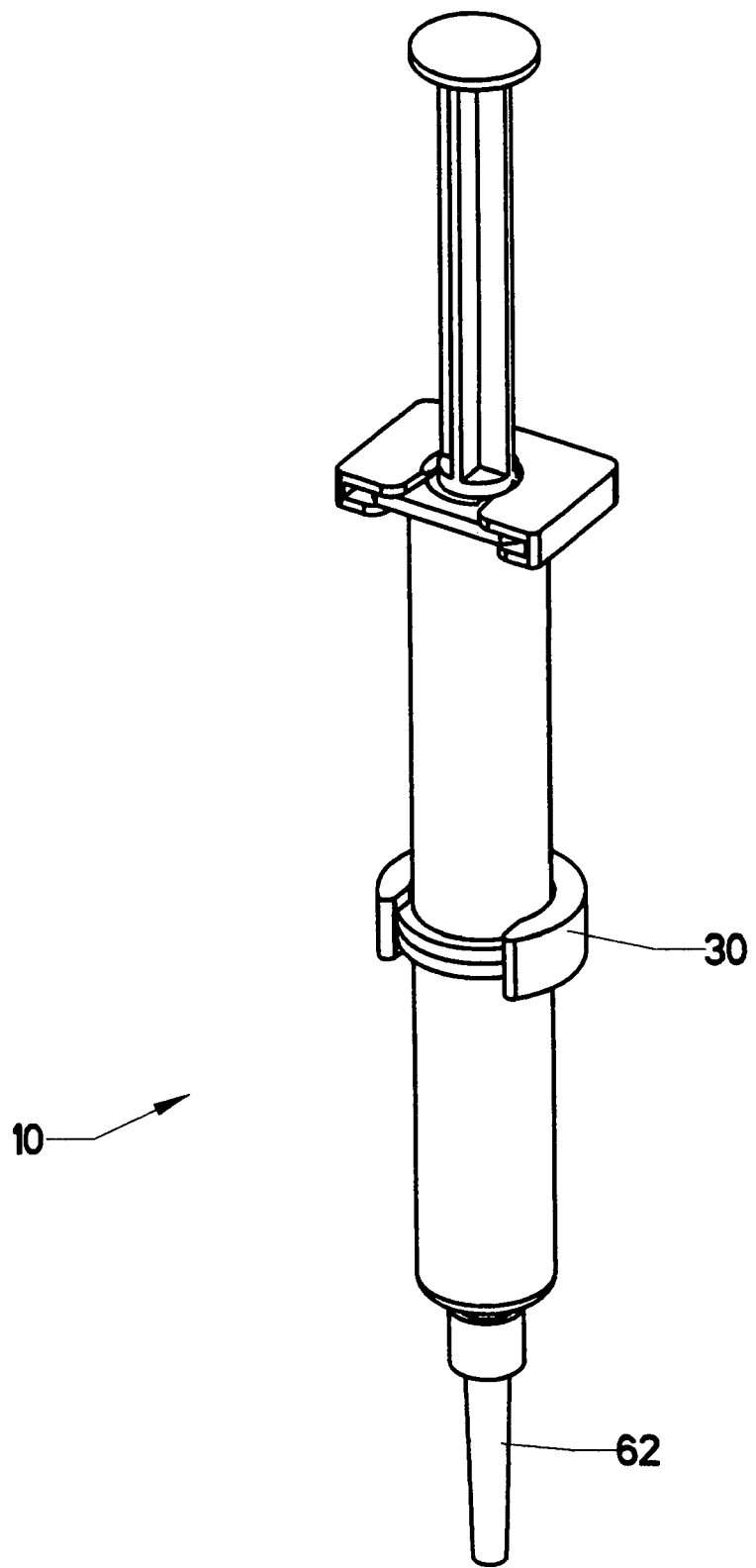
FIG. 7 is a perspective view, showing the use of a linking clip to lock the liquid and powder housings together.

In FIG. 6, liquid assembly 64 has been placed over powder assembly 60, with the two foil seals touching. Linking clip 30 is then locked over flange 22 and flange 24. The linking clip is preferably made of a resilient polymer, sot that once it snaps into place it will hold the liquid and powder assemblies firmly together. FIG. 7 shows the completed mixing syringe 10, with linking clip 30 in position.

Those skilled in the art will know that the two assemblies could be joined using many different techniques. They could, for instance, be glued together. A threaded connection between the two could also be provided. Thus, the linking clip should be understood as being only one example.

Figure 8:
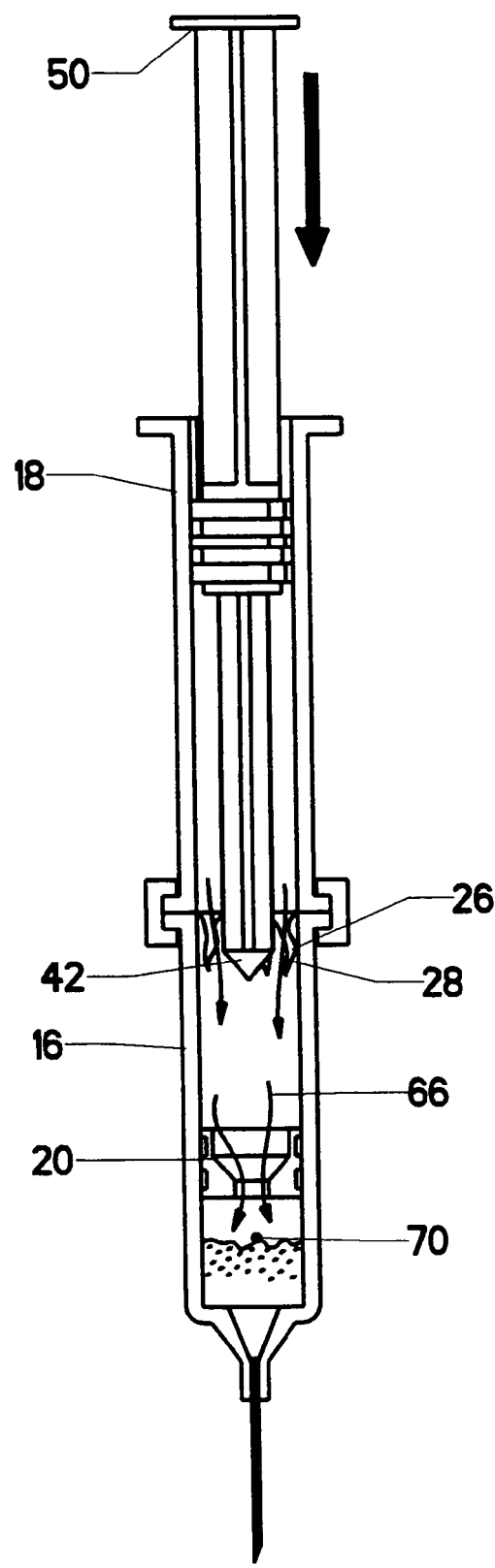
FIG. 8 is a sectional elevation view, showing the operation of the invention.

Once in the state shown in FIG. 7, the mixing syringe is ready for use. FIGS. 8 through 11 illustrate the operation of the device. The user must first hold the syringe approximately upright, as shown in FIG. 8. He or she then presses down on plunger head 50. The reader will recall that at this point vent blocks 40 are occluding vents 46 in secondary piston 44. Thus, the secondary piston pressurizes the gas lying beneath it (and lying on top of the water within the liquid housing). The gas is moderately compressed by the time piercer 42 ruptures foil seal 26 and foil seal 28.

Once the foil seals are ruptured, the liquid within the liquid housing shoots down (under pressure) into powder housing 16. The liquid flows down through primary piston 20 and into mixing chamber 70, where it mixes with the powder. As the user continues depressing the plunger head, vents 46 slide down past vent blocks 40. The compressed air is then able to slide past the secondary piston at a metered rate.

Figure 9:
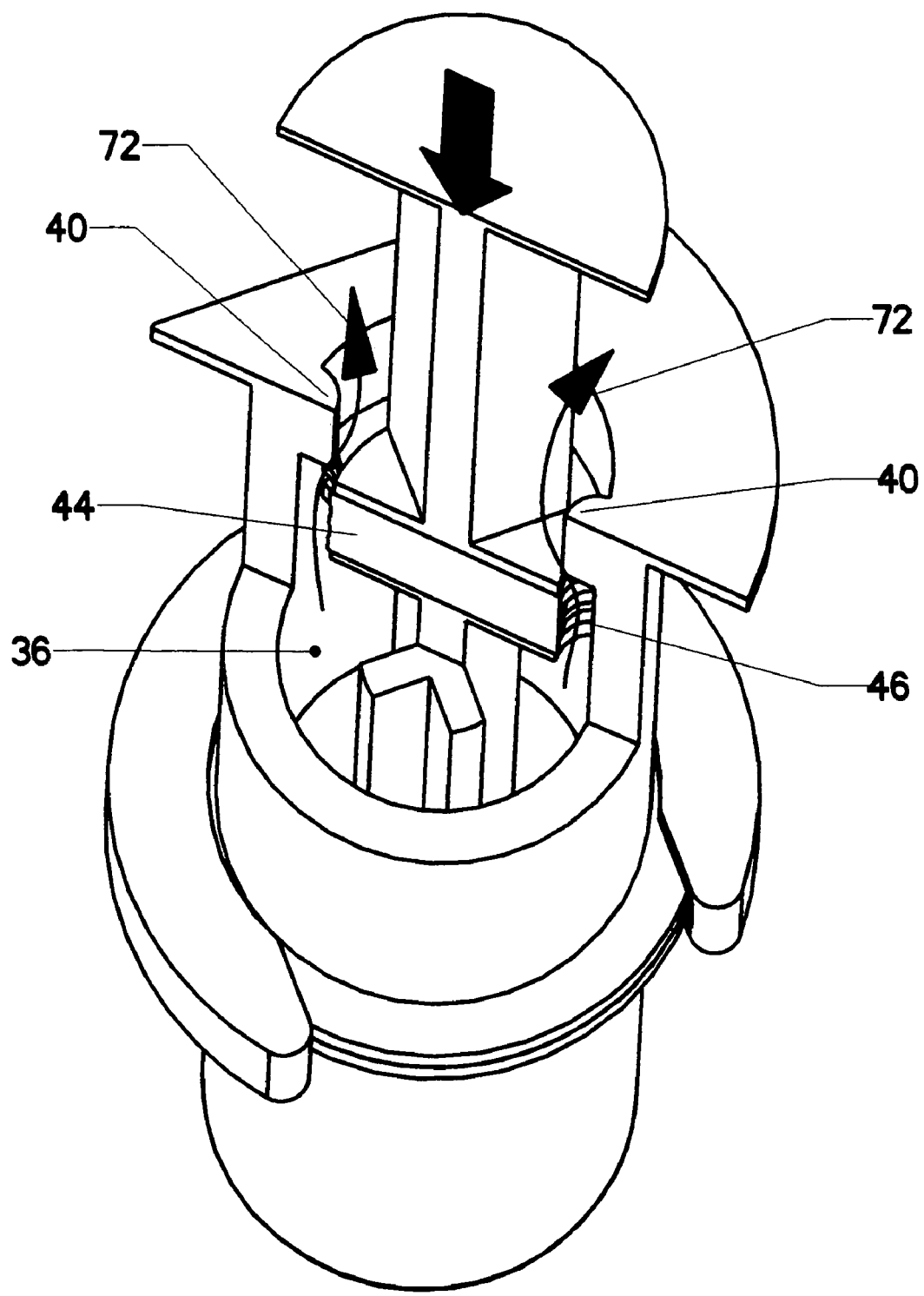
FIG. 9 is a detailed perspective view with a cutaway, showing the operation of the invention.

FIG. 9 shows the secondary piston just as it has traveled past the vent blocks. A cutaway through the liquid housing and the plunger is provided to aid visualization. As the secondary piston is propelled downward, escaping air 72 passes through vents 46. The size of the vents limits the rate at which the user can depress the plunger. In effect, the vent sizing meters the downward rate of travel for the plunger. This is a desired feature, since it allows time for an appropriate amount of liquid to spray downward past primary piston 20.

Figure 10:
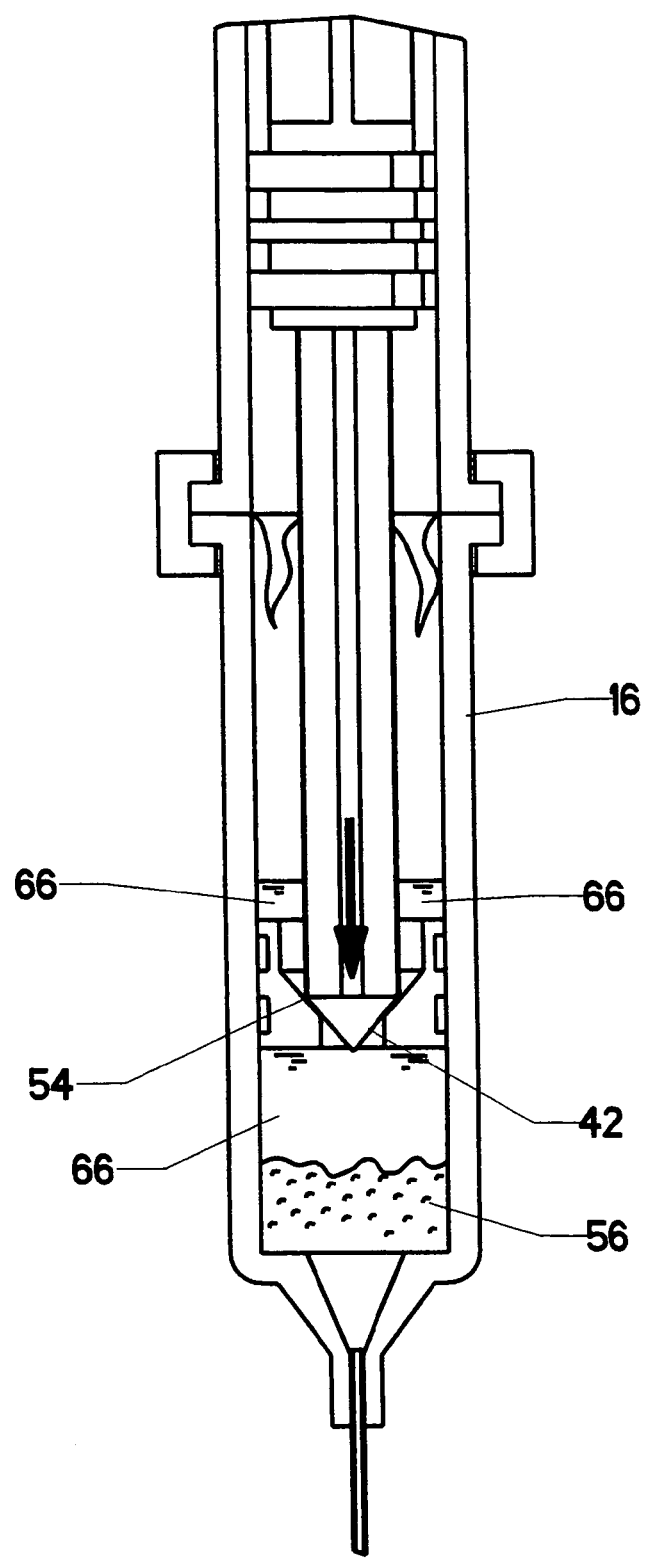
FIG. 10 is a sectional elevation view, showing the operation of the invention.

The user continues depressing the plunger until piercer 42 makes contact with piercer seat 54—as shown in FIG. 10. The user will feel a resistance at this point and should stop depressing the plunger. The liquid and powder housings are preferably made of transparent material so that the user can actually see the piercer seat within the primary piston.

At this point the volume beneath primary piston 20 will be filled with liquid and powder. An additional amount of liquid 66 is often left above primary piston 20. This is true because an excess amount of liquid is preferably employed to ensure complete or near-complete filling of the volume beneath the primary piston.

At this point the fairly violent injection of the liquid into the powder will have frequently produced a good mixture. However, it is advantageous for the user to swirl or shake the syringe to mix any remaining solid clumps. The syringe is then ready for injection.

Figure 11:
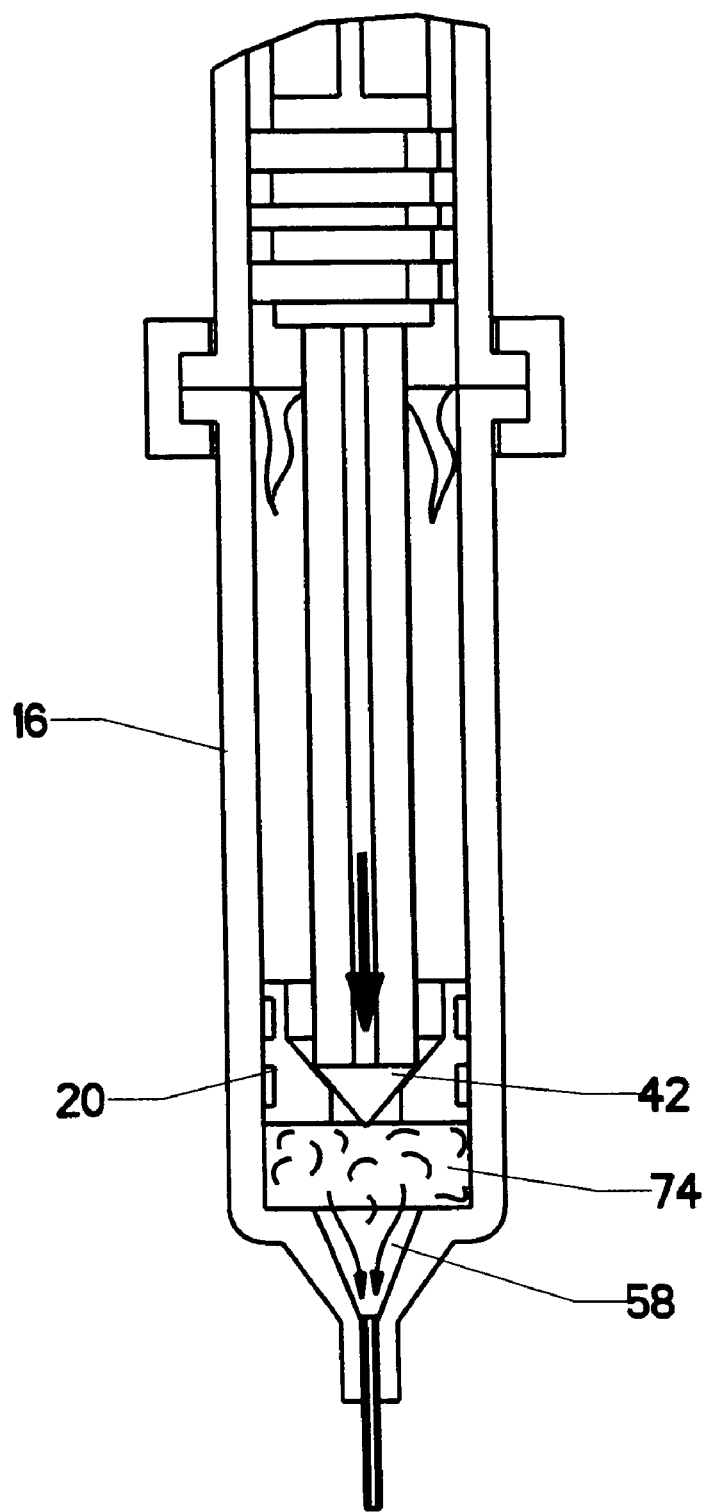
FIG. 11 is a sectional elevation view, showing the operation of the invention.

If the needle cap has not already been removed, it is removed at this point. The volume to be injected is now completely sealed beneath piercer 42 and primary piston 20 (the piercer has sealed the passage through the primary piston). The syringe can be inverted at this point (or placed in any desired orientation). If the plunger is depressed further—as shown in FIG. 11—piercer 42 drives primary piston 20 toward the needle, thereby forcing mixture 74 out through the needle. The user can invert the syringe and force a few drops out through the needle to ensure purging of any air within the mixture. The needle is then inserted into the patient at an appropriate point and the mixture is injected.

The reader will thereby appreciate that the present invention can automate the mixing of a powder into a carrier liquid prior to injection into a patient. The device functions well even after an extended period of storage. This is true because the liquid and the powder are housed in completely separate containers. Even though the containers may be stacked in line, they are still separate. No water will seep into the powder housing, thereby potentially contaminating the powder.

Nor will the orientation of the device during storage affect its utility. Returning to FIG. 2, the reader will recall that powder 56 is initially stored within mixing chamber 70. If the powder housing is inverted (with respect to the position shown in the view), some of the powder may flow through passage 68 and wind up on the opposite side of primary piston 20. This fact will not significantly alter the device's operation. Returning now to FIG. 8, the reader will recall that at the point the foil seals are ruptured, the gas residing above the liquid in the liquid housing has been compressed by the secondary piston's downward travel. When the seals rupture, the liquid is propelled violently down into the powder housing. It swirls around and washes any powder above the primary piston down into the mixing chamber.

This process is not perfect, and a small amount of powder may ultimately remain above the mixing chamber. The vast majority will be mixed, however, and any lost powder will not be significant.

Figure 12:
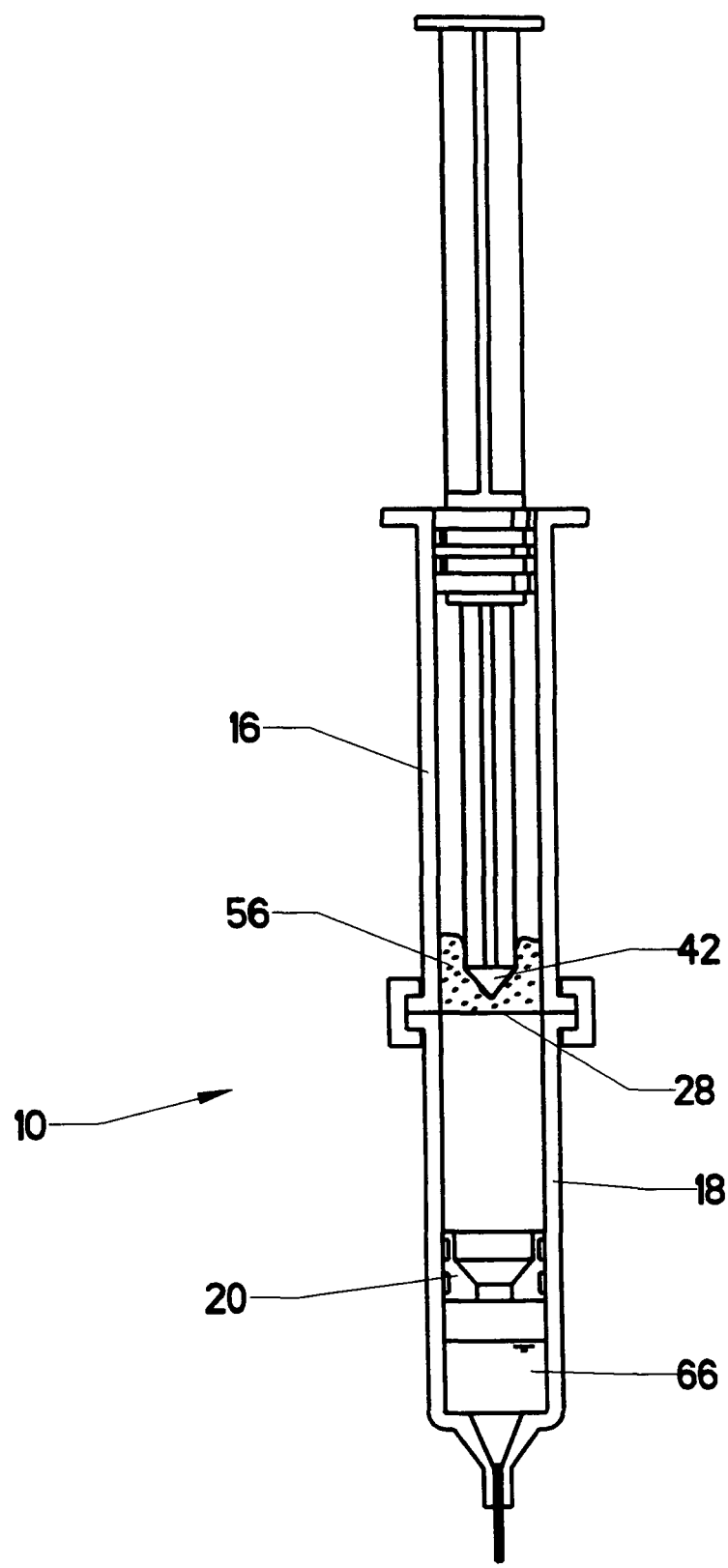
FIG. 12 is a sectional elevation view, showing an alternate embodiment.

The embodiment shown up through FIG. 11 places the liquid housing above the powder housing during the mixing process. While this represents the preferred embodiment, it is obviously not the only possible arrangement. FIG. 12 shows an alternate embodiment in which powder housing 16 is placed above liquid housing 18. When the piercer pierces the foil seal, the powder is propelled downward into the liquid housing. The user must generally shake the syringe to ensure that all the powder passes through the primary piston and down to liquid 66. The plunger is depressed until the piercer seals the primary piston. The syringe is then swirled and the mixture is injected.

Although the preceding description contains significant detail, it should not be construed as limiting the scope of the invention but rather as providing illustrations of the preferred embodiments of the invention. Thus, the scope of the invention should be fixed by the following claims, rather than by the examples given.

Having described our invention, we claim:

1. A method for combining a liquid and a powder to form a mixture, comprising:
   a. providing an enclosure;
   b. providing a primary piston, slidably mounted within said enclosure, wherein said primary piston divides said enclosure into a first volume on a first side of said primary piston and a second volume on a second side of said primary piston;
   c. providing a volume of liquid initially located within said first volume;
   d. providing a volume of powder initially located within said second volume;
   e. providing a passage from said first side of said primary piston to said second side of said primary piston;
   f. providing a removable barrier preventing movement of said liquid through said passage;
   g. providing a plunger movably mounted within said enclosure, wherein the motion of said plunger opens said removable barrier, thereby allowing said volume of liquid to flow through said passage into said volume of powder, thereby forming said mixture;
   h. moving said plunger, thereby opening said removable barrier and forcing said liquid into said second volume and into said powder, thereby forming said mixture; and
   i. forming a seal between a portion of said plunger and said primary piston once said mixture is formed so that further motion of said plunger propels said sealed primary piston into said second volume.

2. A method for combining a liquid and a powder as recited in claim 1, wherein said step of sealing said passage after said liquid is forced through said passage comprises:
  a. providing a first sealing surface on said plunger;
  b. providing a second sealing surface on said primary piston surrounding said passage on a first side of said primary piston facing said first volume; and
  c. pressing said first sealing surface against said second sealing surface to seal said passage.

3. A method for combining a liquid and a powder as recited in claim 2, wherein said first sealing surface is a male conical surface and said second sealing surface is a female conical surface.

4. A method for combining a liquid and a powder as recited in claim 2, wherein said first sealing surface is a male spherical surface and said second sealing surface is a female spherical surface.

5. A method for combining a liquid and a powder as recited in claim 1, further comprising providing said plunger with a secondary piston slidably mounted within said first volume.

6. A method for combining a liquid and a powder as recited in claim 1, further comprising:
  a. providing said secondary piston with at least one air vent; and
  b. metering the escape of gas contained within said first volume through said at least one air vent.

7. A method for combining a liquid and a powder to form a mixture, comprising:
  a. providing an enclosure;
  b. providing a primary piston, slidably mounted within said enclosure, wherein said primary piston divides said enclosure into a first volume on a first side of said primary piston and a second volume on a second side of said primary piston;
  c. providing a volume of powder initially located within said first volume;
  d. providing a volume of liquid initially located within said second volume;
  e. providing a passage from said first side of said primary piston to said second side of said primary piston;
  f. providing a removable barrier preventing movement of said powder through said passage;
  g. providing a plunger movably mounted within said enclosure, wherein the motion of said plunger opens said removable barrier, thereby allowing said volume of liquid to flow through said passage into said volume of powder thereby forming said mixture;
  h. moving said plunger, thereby opening said removable barrier and forcing said powder into said second volume and into said liquid, thereby forming said mixture; and
  i. forming a seal between a portion of said plunger and said primary piston once said mixture is formed so that further motion of said plunger propels said sealed primary piston into said second volume.

8. A method for combining a liquid and a powder as recited in claim 7, wherein said step of sealing said passage after said powder is forced through said passage comprises:
  a. providing a first sealing surface on said plunger;
  b. providing a second sealing surface on said primary piston surrounding said passage on a first side of said primary piston facing said first volume; and
  c. pressing said first sealing surface against said second sealing surface to seal said passage.

9. A method for combining a liquid and a powder as recited in claim 8, wherein said first sealing surface is a male conical surface and said second sealing surface is a female conical surface.

10. A method for combining a liquid and a powder as recited in claim 8, wherein said first sealing surface is a male spherical surface and said second sealing surface is a female spherical surface.

11. A method for combining a liquid and a powder as recited in claim 7, further comprising providing said plunger with a secondary piston slidably mounted within said first volume.

12. A method for combining a liquid and a powder as recited in claim 7, further comprising:
  a. providing said secondary piston with at least one air vent; and
  b. metering the escape of gas contained within said first volume through said at least one air vent.

13. A method for combining a liquid and a powder to form a mixture, comprising:
  a. providing an enclosure;
  b. providing a primary piston, slidably mounted within said enclosure, wherein said primary piston divides said enclosure into a first volume on a first side of said primary piston and a second volume on a second side of said primary piston;
  c. providing a volume of liquid initially located within said first volume;
  d. providing a volume of powder initially located within said second volume;
  e. providing a passage from said first side of said primary piston to a second side of said primary piston;
  f. providing a removable barrier preventing movement of said liquid through said passage;
  g. opening said removable barrier;
  h. forcing said liquid through said passage into said second volume, thereby forming said mixture;
  i. providing a plunger movably mounted within said enclosure, wherein the motion of said plunger opens said removable barrier, thereby allowing said volume of liquid to flow through said passage into said volume of powder, thereby forming said mixture; and
  j. after forcing said liquid through said passage into said second volume sealing said plunger against said primary piston.

14. A method for combining a liquid and a powder to form a mixture as recited in claim 13, further comprising:
  a. after said liquid has been forced through said passage, sealing said passage; and
  b. using said primary piston to force said mixture out of said second volume.

15. A method for combining a liquid and a powder as recited in claim 14, wherein said step of sealing said passage after said liquid is forced through said passage comprises:
  a. providing a first sealing surface on said plunger;
  b. providing a second sealing surface on said primary piston surrounding said passage on a first side of said primary piston facing said first volume; and
  c. pressing said first sealing surface against said second sealing surface to seal said passage.

16. A method for combining a liquid and a powder as recited in claim 15, wherein said first sealing surface is a male conical surface and said second sealing surface is a female conical surface.

17. A method for combining a liquid and a powder as recited in claim 15, wherein said first sealing surface is a male spherical surface and said second sealing surface is a female spherical surface.

18. A method for combining a liquid and a powder as recited in claim 15, further comprising providing said plunger with a secondary piston slidably mounted within said first volume.

* * * * *